(12) United States Patent
Sunami et al.

(10) Patent No.: US 10,317,283 B2
(45) Date of Patent: Jun. 11, 2019

(54) SPECTRUM MEASUREMENT METHOD USING FOURIER TRANSFORM TYPE SPECTROSCOPIC DEVICE

(71) Applicant: JASCO CORPORATION, Tokyo (JP)

(72) Inventors: Tetsuji Sunami, Tokyo (JP); Takashi Shimamura, Tokyo (JP); Norio Wakimoto, Tokyo (JP); Jun Koshobu, Tokyo (JP)

(73) Assignee: JASCO CORPORATION, Tokyo (JP)

( * ) Notice: Subject to any disclaimer, the term of this patent is extended or adjusted under 35 U.S.C. 154(b) by 0 days.

(21) Appl. No.: 16/075,346

(22) PCT Filed: Feb. 2, 2017

(86) PCT No.: PCT/JP2017/003726
§ 371 (c)(1),
(2) Date: Aug. 3, 2018

(87) PCT Pub. No.: WO2017/135356
PCT Pub. Date: Aug. 10, 2017

(65) Prior Publication Data
US 2019/0041268 A1 Feb. 7, 2019

(30) Foreign Application Priority Data
Feb. 4, 2016 (JP) .................. 2016-020084

(51) Int. Cl.
*G01J 5/02* (2006.01)
*G01J 3/45* (2006.01)
(Continued)

(52) U.S. Cl.
CPC ................. *G01J 3/45* (2013.01);
*G01J 3/28* (2013.01); *G01J 3/453* (2013.01);
*G01N 21/00* (2013.01);
(Continued)

(58) Field of Classification Search
CPC .... G01J 3/45; G01J 3/28; G01J 3/0297; G01J 3/453; G01N 21/35; G01N 2021/3595; G01N 21/31; G01N 21/25; G01N 21/00
See application file for complete search history.

(56) References Cited

U.S. PATENT DOCUMENTS 5,039,222 A 8/1991 Izumi
9,109,869 B2 8/2015 Hirao
(Continued)

FOREIGN PATENT DOCUMENTS

JP 02-27226 A 1/1990
JP 06-03189 A 1/1994
(Continued)

OTHER PUBLICATIONS

U.S. Appl. No. 16/089,146 to Noriaki Soga et al., filed Sep. 27, 2018.
(Continued)

*Primary Examiner* — Kiho Kim
(74) *Attorney, Agent, or Firm* — Greenblum & Bernstein, P.L.C.

(57) ABSTRACT

A method for measuring spectrum by Fourier-transforming an interferogram of an infrared interference wave acquired with an interferometer, including a step of over-sampling intensity signals of the interference wave at positions (D1, D2, . . . ) of a movable mirror set on the basis of a wavelength $\lambda 1$ of a semi-conductor laser, and a step of interpolating intensity signals (I1', I2', . . . ) that would be obtained when the interference wave is sampled at positions (D1', D2', . . . ) of the movable mirror set on the basis of a wavelength $\lambda 0$ of a He—Ne laser, by using the over-sampled intensity signals (I1, I2, . . . ), for calculating the spectrum with the interferogram based on the interpolated intensity signals (I1', I2', . . . ) and for an efficient use of conventional
(Continued)

stored spectrum data which are measured based on the wavelength λ0.

8 Claims, 6 Drawing Sheets

(51) Int. Cl.
    *G01N 21/35* (2014.01)
    *G01J 3/28* (2006.01)
    *G01J 3/453* (2006.01)
    *G01N 21/31* (2006.01)
    *G01N 21/25* (2006.01)
    *G01N 21/00* (2006.01)
    *G01J 3/02* (2006.01)
(52) U.S. Cl.
    CPC ............ *G01N 21/25* (2013.01); *G01N 21/31* (2013.01); *G01N 21/35* (2013.01); *G01J 3/0297* (2013.01); *G01N 2021/3595* (2013.01)

(56) References Cited

U.S. PATENT DOCUMENTS

| | | | |
|---|---|---|---|
| 9,194,744 B2 * | 11/2015 | Yost | G01J 3/28 |
| 9,804,086 B2 * | 10/2017 | Case | G01N 21/3577 |
| 10,066,992 B2 * | 9/2018 | Ando | G01J 3/28 |
| 2003/0146386 A1 | 8/2003 | Nagoshi et al. | |
| 2005/0073690 A1 | 4/2005 | Abbink et al. | |
| 2006/0238768 A1 * | 10/2006 | Brorson | G01J 3/4535 356/451 |
| 2006/0262316 A1 | 11/2006 | Baney | |
| 2009/0112500 A1 | 4/2009 | Yerazunis et al. | |
| 2013/0222790 A1 | 8/2013 | Hirao | |

FOREIGN PATENT DOCUMENTS

| | | |
|---|---|---|
| JP | 06-03192 A | 1/1994 |
| JP | 10-90065 A | 4/1998 |
| JP | 2003-227754 A | 8/2003 |
| JP | 2006-125971 A | 5/2006 |
| JP | 2009-103686 A | 5/2009 |
| JP | 2013-250127 A | 12/2013 |
| WO | 2012/056813 A1 | 5/2012 |
| WO | 2014/199888 A1 | 12/2014 |

OTHER PUBLICATIONS

International Search Report issued in WIPO Patent Application No. PCT/JP2017/003726, dated Apr. 4, 2017.

* cited by examiner

SPECTRUM MEASUREMENT METHOD USING FOURIER TRANSFORM TYPE SPECTROSCOPIC DEVICE

RELATED APPLICATIONS

This application claims the priority of Japanese Patent Application No. 2016-020084 filed on Feb. 4, 2016, the disclosure of which is incorporated herein by reference in its entirety.

FIELD OF THE INVENTION

The present invention relates to a measurement method of a spectrum when a Fourier transform type spectroscopic device comprises a general-purpose laser as a position reference laser of a movable mirror.

BACKGROUND OF THE INVENTION

In Fourier transform type spectroscopic devices, interferometers are used to detect interference waves of measurement light in a non-dispersive method, and interference waves are Fourier-transformed by a computer to obtain spectrum data of measurement light. Due to formation of interference waves of measurement light, each wavenumber components of measurement light based on intensity signals of interference waves composed of total wavenumber component of measurement light can be calculated by Fourier transform. Fourier transform spectroscopy is suitable for high speed measurement, and is the mainstream in infrared spectrophotometers. It is widely used as Fourier transform type infrared spectrophotometers (FTIR) (refer to Patent Literature 1).

The interferometer used in this spectroscopic device is generally a Michelson interferometer, and comprises a semi-transparent mirror and two reflection mirrors (fixed mirror and movable mirror). The movable mirror makes the optical path difference of the interferometer variable, and the position of the movable mirror and the optical path difference are in a one-to-one relation. The interferometer generates interference waves of measurement light that correspond to the optical path difference. By detecting intensity of this interference wave, an interferogram (interference curve) having the optical path difference in a horizontal axis and the intensity signal in a vertical axis can be obtained. The computer calculates the spectrum data by Fourier-transforming the interferogram data.

The timing of detecting the interference wave is generally determined by referring to the position of the movable mirror by a laser light. It is referred to as a position reference laser herein. The position reference laser irradiates the laser light to the movable mirror, and the interferometer forms a laser interference wave based on its reflection light. Usually, a laser detector detects the interference wave of the measurement light when the intensity signal of the laser interference wave becomes zero. That is, the detection timing depends on a wavelength λ of the position reference laser.

On the other hand, in an FTIR of Patent Literature 1, a ΔΣ type AD converter AD-converts the interferogram signal to improve S/N. This ΔΣ type AD converter uses a basic clock that is asynchronous with moving speed of the movable mirror to AD-convert the interferogram signal from the infrared detector and the laser interference wave signal from the laser detector simultaneously. Then, the computer interpolates the interferogram signal that is AD-converted so that the angle variation of the laser interference signal is constant, and thus obtains the interferogram that is synchronized with the movement of the movable mirror.

CITATION LIST

Patent Literature

PATENT LITERATURE 1: Japanese Unexamined Patent Publication No. JP2006-125971

DISCLOSURE OF THE INVENTION

Problem to be Solved by the Invention

In general, Fourier transform type spectroscopic devices compare a large amount of spectrum data stored in databases with measurement spectrum data to identify sample components. At present, stored spectrum data are measured by spectroscopes that use He—Ne lasers (also referred to as reference laser) for position reference of the movable mirror. The spectroscopic device of Patent Literature 1 comprises a He—Ne laser as the position reference laser too.

On the other hand, spectroscopic devices that use semi-conductor lasers (also referred to as general-purpose lasers) instead of He—Ne lasers are increasing because semi-conductor lasers are low in cost and power consumption, although they are inferior to He—Ne laser in wavelength resolution.

However, when spectroscopic devices having semi-conductor lasers for position reference of the movable mirror perform spectrum measurement, there were following problems.

(1) Measurement spectrum data do not match spectrum data measured by a spectroscopic device that uses a conventional He—Ne laser because the wavelengths of position reference lasers are different. When the wavelengths of each of position reference lasers of two Fourier transform type spectroscopic devices are different, each spectrum data cannot be compared because identity of spectrum data obtained by each spectroscope cannot be secured. Therefore, it was difficult to use numerous spectrum data that are stored.

(2) Validation method for the wavelength of the semi-conductor lasers needed to be established for cases when the wavelength of the semi-conductor lasers changes over time (or changes by environmental dependence).

The present invention is made in view of the above-mentioned circumstances, and the first object is to provide a spectrum measurement method that is capable of comparing with conventional stored spectrum data even if the wavelength of the position reference laser of the movable mirror is different. The second object is to establish a validation method for the wavelength of the position reference laser for cases when the wavelength of the position reference laser of the movable mirror changes over time (or changes by environmental dependence).

Means to Solve the Problem

To achieve the above-mentioned objects, a method according to the present invention is a method comprising: a step of obtaining an interferogram of a measurement light with an interferometer, and a step of Fourier-transforming the interferogram into a spectrum of a sample, wherein the step of obtaining the interferogram comprises:
a step of moving a movable mirror that constitutes the interferometer at a constant speed, a step of over-sampling intensity signals (I1, I2, . . . ) of an interference wave of the measurement light at positions (D1, D2, . . . ) of the movable mirror set on the basis of a wavelength λ1 by using a general-purpose laser of the wavelength λ1 as a position reference laser of the movable mirror, and a step of interpolating intensity signals (I1', I2', . . . ) that would be obtained when the interference wave of the measurement light is sampled at positions (D1', D2', . . . ) of the movable mirror set on the basis of a wavelength λ0 that is different from the wavelength λ1, based on the over-sampled intensity signals (I1, I2, . . . ) by a computer, wherein the interferogram comprising the intensity signals (I1', I2', . . . ) of the interference wave of the measurement light at positions (D1', D2', . . . ) of the movable mirror set on the basis of the wavelength λ0 is obtained.

"Each position of the movable mirror set on the basis of the wavelength" is each one of positions at fixed intervals from a position of the movable mirror where optical difference of the interferometer becomes zero. The fixed interval is a length of N times (or one Nth of) the wavelength λ1. N is an integer other than zero. Further, "over-sampling" indicates that a sampling number which shows positions set on the basis of the wavelength λ1 is larger than a sampling number which shows positions set on the basis of the wavelength λ0 when a moving range of the movable mirror is the same.

The step of interpolating preferably includes calculating the intensity signal (for example I2') of the interference wave at the position of the movable mirror set on the basis of the wavelength λ0, based on each intensity signals (for example I5 and I6) that are over-sampled at sampling positions (for example D5 and D6) that are the closest and the second closest to the position (for example D2') of the movable mirror set on the basis of the wavelength λ0 by the computer.

The step of interpolating of the present invention calculates data at a non-sampling position that is different from each sampling position of a plurality of over-sampled data. That is, data at the position of the movable mirror based on a reference laser (for example, a He—Ne laser) are calculated by interpolating from the over-sampled data based on a general-purpose laser (for example, a semi-conductor laser) in the vicinity thereof. Accordingly, the interferogram at a mirror position same as the mirror position when the interferometer samples the signal intensity of the interferogram by using the reference laser as the position reference laser of the movable mirror is calculated. As a result, a spectrum that can be obtained by Fourier-transforming the interferogram calculated by the method of the present invention is substantially identical to a spectrum measured by a spectroscopic device that comprises the reference laser as the position reference laser of the movable mirror.

Further, the inventors has established a method to validate the wavelength λ1 of the general-purpose laser in the following way in case the wavelength λ1 of the general-purpose laser changes minutely to the wavelength λ1' due to change over time (or change by environmental dependence). With respect to measurement spectrum data of a reference sample, the inventors focused on the point that data measured by a conventional method that uses the reference laser and data measured by the method of the present invention that uses the genera-use laser are in a fixed relationship. Similarly, the present inventors considered that a fixed relationship exists when an oscillation wavelength λ1 of the general-purpose laser changes to the wavelength λ1'. That is, with respect to all peak positions (wavenumber) based on a certain wavenumber as a reference among a reference sample spectrum measured from the wavelength λ1 before change, all peak positions (wavenumber) based on a certain wavenumber as a reference among a reference sample spectrum measured from the wavelength λ1' after change move at a same ratio. On the assumption that the oscillation wavelength of the general-purpose laser is not changed, when the computer calculates each spectrum before and after change and compares two spectra, the computer recognizes such the moving of peak positions. Its ratio can be regarded as a wavelength ratio (λ1'/λ1) of the general-purpose laser. In the method of the present invention, the computer obtains the wavelength ratio (λ1'/λ1) from the moving of the peak position of the measurement spectrum, recalculates the wavelength λ1 of the general-purpose laser, and uses the recalculated value of the wavelength λ1 at the step of interpolating of the present invention.

That is, the method of the present invention further comprises a step of validating the wavelength λ1 of the general-purpose laser, wherein the step of validating comprises:

a step of measuring a spectrum of a reference sample by an interferometer having a reference laser of a wavelength λ0 as the position reference laser, a step of measuring a spectrum of the reference sample by an interferometer having a general-purpose laser of a wavelength λ1 as the position reference laser, and a step of calculating the wavelength λ1 of the general-purpose laser based on an average value of the change ratio of each peak position for a plurality of peaks in the spectrum, wherein the change ratio of each peak position is read out by comparing two spectra measured at two steps of measuring.

Further, the inventors focused on the point that if the peak position of the measurement spectrum data of the reference sample measured by the reference laser or the general-purpose laser is memorized in the spectroscopic device, the spectroscopic device can confirm variation of the oscillation wavelength of the general-purpose laser by suitably measuring the spectrum of the reference sample by the general-purpose laser and confirming the moving of the peak position thereafter. When variation of the oscillation wavelength is confirmed, the spectroscopic device preferably performs the above-mentioned validation method of the wavelength.

That is, the method of the present invention comprises:

a step of storing the peak positions of the spectrum of the reference sample measured by the interferometer having the general-purpose laser of the wavelength λ1 to a memory means; and a step of comparing the stored peak position of the spectrum of the reference sample and the peak position of the spectrum of the reference sample measured afterwards, wherein the step of validating is preferably performed when the peak positions of the two spectra are changed.

Further, a method according to the present invention comprises a step of obtaining an interferogram of a measurement light with an interferometer, and a step of Fourier-transforming the interferogram into a spectrum of a sample, wherein the step of obtaining the interferogram comprises:

a step of moving a movable mirror that constitutes the interferometer at a constant speed, and a step of sampling intensity signals (I1', I2', . . . ) of an interference wave of the measurement light at positions (D1', D2', . . . ) of the movable mirror set on the basis of a wavelength λ0 that is different from a wavelength λ1 by using a general-purpose laser of the wavelength λ1 as a position reference laser of the movable mirror, wherein the interferogram comprised of the intensity signals (I1', I2', . . . ) of the interference wave of the measurement light at each sampling positions (D1', D2', . . . ) set on the basis of the wavelength λ0 is obtained.

In the step of sampling, each position of the movable mirror at a timing of which a delay time respectively determined for each position of the movable mirror passes from a timing when the movable mirror reaches each position set on the basis of the wavelength λ1 is used as the each sampling position (D1', D2', . . . ) set on the basis of the wavelength λ0.

Further, in the step of sampling, each position of the movable mirror obtained by adding a certain length to each position set on the basis of the wavelength λ1 is used as the each sampling position (D1', D2', . . . ) set on the basis of the wavelength λ0, wherein the certain length is gained by multiplying a moving speed of the movable mirror by a delay time respectively determined for each position of the movable mirror.

Further, the method of the present invention comprises a step of detecting the moving speed of the movable mirror for each point when the movable mirror reaches each position (D1, D2, . . . ) set on the basis of the wavelength λ1, wherein, in the step of sampling, the each sampling position (D1', D2', . . . ) set on the basis of the wavelength λ0 is preferably calculated by the detected moving speed.

Effect of the Invention

According to the method of the present invention constituted as above:

(1) Even if the Fourier transform type spectroscopic device has the general-purpose laser of the wavelength λ1 as the position reference laser of the movable mirror, the spectrum obtained by this spectroscopic device becomes identical or substantially identical to the spectrum measured by the conventional spectroscopic device having the reference laser. Therefore, even if the spectrum data stored in databases is the spectrum measured by the reference laser having the wavelength λ0, the spectrum obtained by the general-purpose laser having the wavelength λ1 and the existing spectrum data can still be compared, so that the existing databases can be effectively used.

(2) The spectroscopic device or a user can easily determine the presence or absence of variation of the oscillation wavelength of the general-purpose laser, and validation of the wavelength can be executed. If the spectroscopic device executes such obtaining method of the interferogram and such calibrating method of the wavelength, S/N ratio is maintained at a same level as the conventional measurement data. Further, by validating the wavelength, the oscillation wavelength of the general-purpose laser can easily be made closer to an ideal value (true value).

(3) When the spectroscopic device has the general-purpose laser having different wavelengths between spectroscopic devices or even when the general-purpose laser of the spectroscopic device is exchanged to the general-purpose laser having different wavelength, identity of measurement data can be secured.

(4) Since the spectroscopic device has the semi-conductor laser as the general-purpose laser, power consumption and cost are reduced compared to the spectroscopic device having the conventional He—Ne laser.

DESCRIPTION OF REFERENCE NUMBERS

12 Interferometer
14 Infrared detector
16 Interferogram obtaining means
18 Fourier transform means
24 Movable mirror
30 General-purpose laser
32 Laser detector
34 Position detecting means
38 Memory
100 Fourier transform type spectrophotometer

BEST MODE FOR CARRYING OUT THE INVENTION

Hereinbelow, preferable embodiments of the present invention are described with reference to the figures.

First Embodiment

Figure 1:
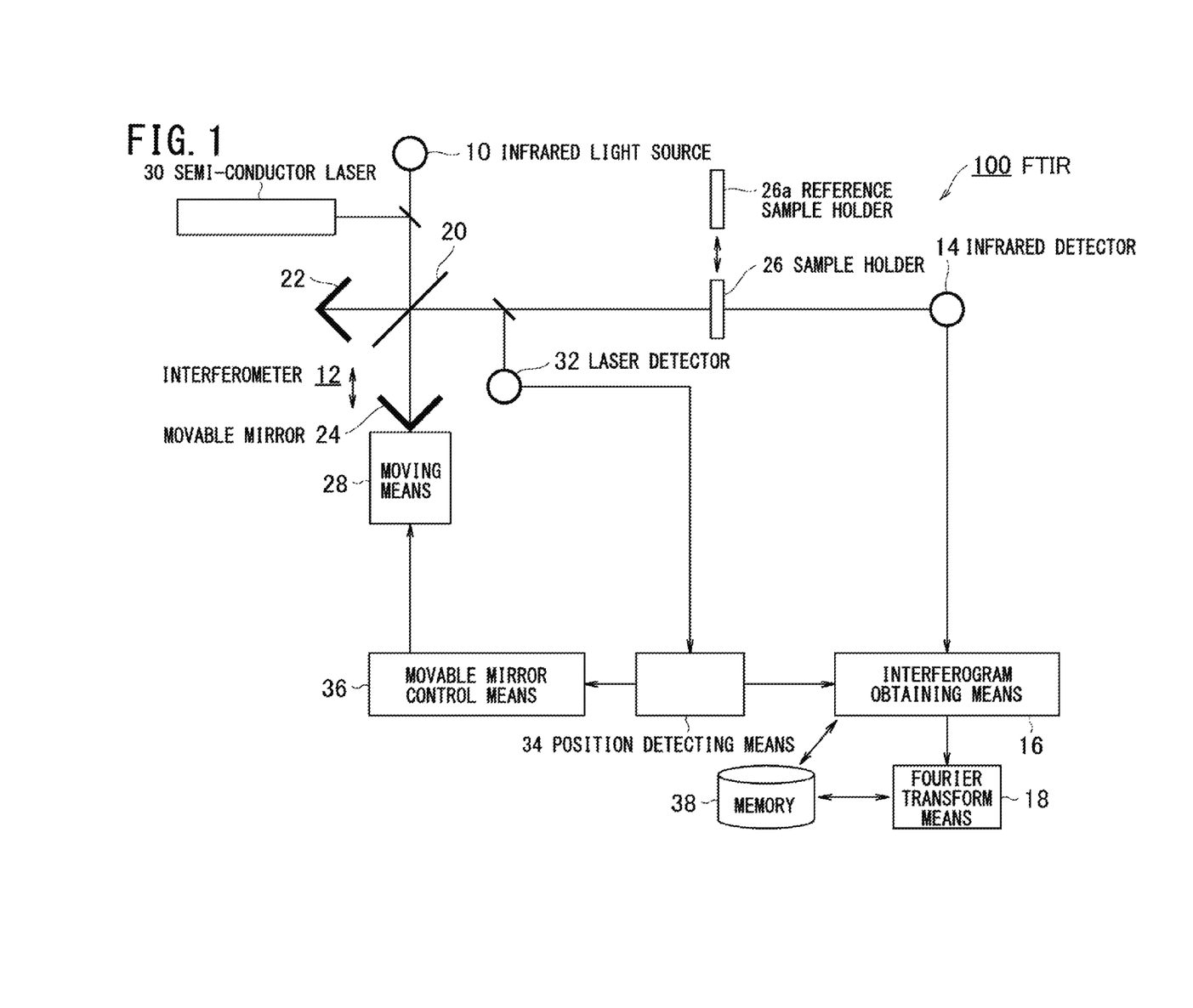
FIG. 1 is a schematic drawing of a Fourier transform type spectroscopic device according to an embodiment of the present invention.

FIG. 1 shows a schematic configuration of a Fourier transform type infrared spectrophotometer (FTIR) 100. The spectroscopic device 100 comprises: an infrared light source 10; an interferometer 12 that forms an infrared interference wave; an infrared detector 14 that outputs an intensity signal of the interference wave obtained by irradiating the infrared interference wave to a sample; an interferogram obtaining means 16 that obtains an interferogram by processing the detected intensity signal; and a Fourier transform means 18 that Fourier-transforms the interferogram data to calculate a measurement spectrum data. Usually, the interferogram obtaining means 16 and the Fourier transform means 18 are constituted of micro-computers incorporated to the spectroscopic device, personal computers separated from the spectroscopic device, or the like.

The interferometer 12 has a light flux splitting part 20 that splits infrared light into two ways, a fixed mirror 22 and a movable mirror 24 which respectively reflect the splitted light, and combines two light fluxes having different optical path lengths to generate an infrared interference wave. The movable mirror 24 is provided to be movable in a direction approaching the light flux splitting part 20 and a direction away from the same. A moving means 28 of the movable mirror is a voice coil motor, for example. The optical path difference of the two light fluxes changes as the movable mirror 24 moves, so that the infrared interference wave is modulated. The infrared interference wave irradiates a sample in a sample holder 26 provided between the light flux splitting part 20 and the infrared detector 14. The infrared detector 14 receives the infrared interference wave from the sample, and outputs its intensity signal.

To obtain position information of the movable mirror 24 by a laser light, the interferometer 12 further comprises a semi-conductor laser 30 for position reference, and a laser detector 32 that detects a laser interference wave. In the present embodiment, the interferometer 12 also acts as the laser interferometer, and the laser light (also called monochromatic light) from the semi-conductor laser 30 is guided to the same optical path as the infrared light. The interferometer 12 generates the laser interference wave as the movable mirror 24 moves, and the laser detector 32 outputs the intensity signal of the laser interference wave. The spectroscopic device 100 may comprise an exclusive laser interferometer that is provided separately from the interferometer 12.

The FTIR of FIG. 1 further comprises: a position detecting means 34 that outputs position information of the movable mirror 24 based on the intensity signal of the laser interference wave; a movable mirror control means 36 that executes speed control of the movable mirror 24 based on the position information, especially its constant speed control; and a memory 38 that stores a set value $\lambda 1$ of the wavelength of the semi-conductor laser 30. The position detecting means 34 counts intensity change of the laser interference wave accompanied by the movement of the movable mirror 24 to obtain position information of the movable mirror 24. Its position information is transmitted to the movable mirror control means 36 and the interferogram obtaining means 16. The interferogram obtaining means 16 obtains an interferogram (interference curve) based on the intensity signal of the infrared interference wave and position information of the movable mirror 24.

It is preferable that the sample holder 26 is provided to be changed with a reference sample holder 26a suitably. Alternatively, an optical path switching part may be provided such that the optical path that guides the infrared interference wave from the interferometer 12 to the sample holder 26 can be switched to an optical path that guides the infrared interference wave from the interferometer 12 to the reference sample holder 26a. And the memory 38 is preferably provided to store a reference spectrum data of a reference sample measured by the spectroscopic device 100. Further, the memory 38 is preferably provided to store a reference spectrum data measured by a conventional spectroscopic device having the He—Ne laser.

<Conventional Spectrum Measurement Method>

Figure 5A:
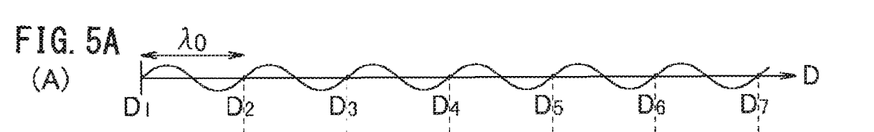
FIG. 5A is a diagram to schematically describe a conventional Fourier transform type spectroscopy, and is a graph showing intensity signals of interference waves of He—Ne lasers.
Figure 5B:
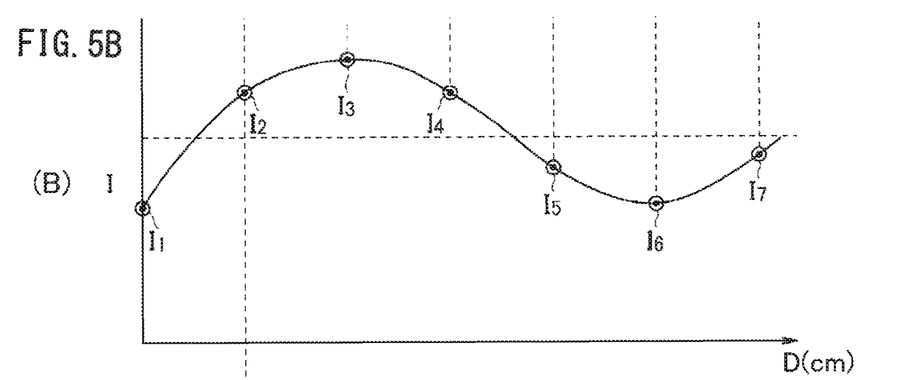
FIG. 5B is a graph showing intensity signals of infrared interference waves that are sampled based on the laser intensity signals of FIG. 5A.

Conventional spectrum measurement method is described with reference to FIGS. 5A to 5D. FIG. 5A shows an intensity signal of an interference wave of the He—Ne laser. The horizontal axis is the position of the movable mirror, namely the optical path difference D. Based on an alternating current component of the detected laser interference wave, a command signal for sampling is generated at each position (D1, D2, . . . ) of the movable mirror for each wavelength $\lambda 0$. FIG. 5B shows an interferogram, namely intensity signals (I1, I2, . . . ) of the infrared interference wave sampled at the above-mentioned positions.

Figure 5C:
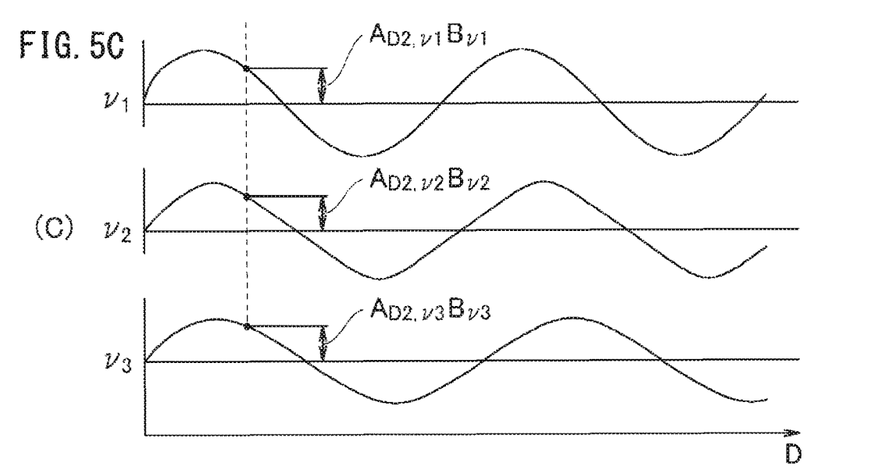
FIG. 5C is a graph showing intensity signals of interference waves comprised of infrared light having differing wavenumbers of ν1 to ν3.
Figure 5D:
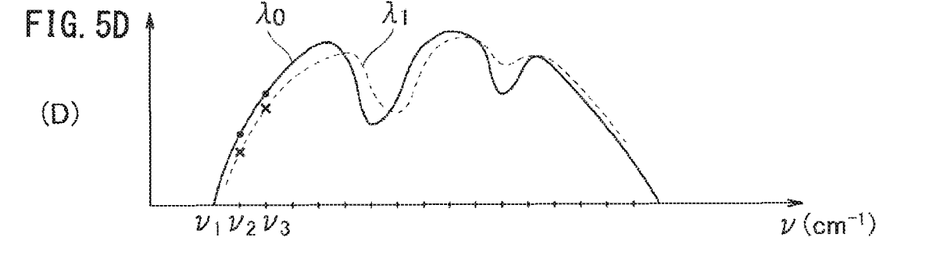
FIG. 5D is a graph showing calculated spectrum data.

Fourier transform spectroscopy is a method that Fourier-transforms an interferogram data into spectrum data (curve of $\lambda 0$) as shown in FIG. 5D. With reference to FIG. 5C, concept of Fourier transform is schematically described herein.

The interference wave composed of the infrared light of a wavenumber v1 is shown by an intensity curve of v1 in FIG. 5C. Similarly, infrared interference waves of different wavenumbers v2, v3, . . . are shown by intensity curves v2, v3, . . . in FIG. 5C. If the interferogram of FIG. 5B is considered to be an intensity signal of an interference wave composed of an infrared light in a range of wavenumbers v1 to vN, the interferogram of FIG. 5B is regarded as one which each intensity curve of FIG. 5C are overlapped. To be more simple, an amplitude of the intensity curve v1 at an optical path difference D2 is expressed by multiplying an intensity $A_{D2, v1}$ of the interference wave at the optical path difference D2 by an absorbance $B_{v1}$ of the infrared light of the wavenumber v1 which gives a value of $A_{D2, v1} \cdot B_{v1}$. Further, an amplitude of the intensity curve v2 at the same optical path difference D2 is expressed by multiplying an intensity $A_{D2, v2}$ of the interference wave by an absorbance $B_{v2}$ of the infrared light of the wavenumber v2 which gives a value of $A_{D2, v2} \cdot B_{v2}$. In that case, an interferogram I2 at the optical difference D2 is expressed by an equation of $A_{D2, v1} \cdot B_{v1} + A_{D2, v2} \cdot B_{v2} + A_{D2, v3} \cdot B_{v3} + \ldots$ The interferogram (I1, I2, I3, . . . ) becomes simultaneous equations as follows.

$$I1 = A_{D1,v1} \cdot B_{v1} + A_{D1,v2} \cdot B_{v2} + A_{D1,v3} \cdot B_{v3} + \ldots$$

$$I2 = A_{D2,v1} \cdot B_{v1} + A_{D2,v2} \cdot B_{v2} + A_{D2,v3} \cdot B_{v3} + \ldots$$

$$I3 = A_{D3,v1} \cdot B_{v1} + A_{D3,v2} \cdot B_{v2} + A_{D3,v3} \cdot B_{v3} + \ldots \qquad (1)$$

Fourier transform is a method to determine the solution $B_{v1}, B_{v2}, \ldots$ of the simultaneous equations of the equation (1). In general, it is difficult to determine the true value of a spectrum in Fourier transform spectroscopy, and an approximate solution relatively close to the true value is merely determined. Therefore, when the position reference laser that is a reference of the optical difference D is replaced, to be more specific, when the He—Ne laser ($\lambda 0 = 632.8$ nm) is replaced with the semi-conductor laser ($\lambda 1 = 680$ nm), each position of the movable mirror 24 set on the basis of the wavelength $\lambda 1$, not the wavelength $\lambda 0$ becomes the sampling position of the infrared interference wave, and thus Fourier transform solves a simultaneous equation that is different from the above-mentioned equation (1). Its approximate solution becomes a curve $\lambda 1$ shown with a dashed line in FIG. 5D, for example.

Even if the sample is the same, when the wavelength of the position reference laser is changed, identity of respective spectrum data could not be sufficiently secured, and a method to compare the spectrum data could not be used.

A data processing program of the present embodiment solves the above-mentioned object, and even if the wavelength of the position reference laser is changed, identity of the spectrum data is secured and comparison of the spectrum data becomes possible.

<Data Processing Program>

The data processing program makes the computer that constitutes the interferogram obtaining means 16 and the Fourier transform means 18 to execute the following steps S1 to S4 to obtain spectrum data of the sample.

First of all, in a step S1 (refer to FIG. 2), the interferogram obtaining means 16 obtains a detection timing of the intensity signal of the infrared interference wave based on position information from the position detecting means 34. The detection timing depends on each position of the movable mirror 24 set on the basis of the wavelength $\lambda 11$ of the semi-conductor laser 30. For example, positions (D1, D2, . . . ) at fixed intervals from position of the movable mirror 24 where the optical difference D of the interferometer 12 becomes zero are set as sampling positions. This fixed interval is preferably N times (or one Nth of) the wavelength $\lambda 1$. N is an integer other than zero.

Figure 2:
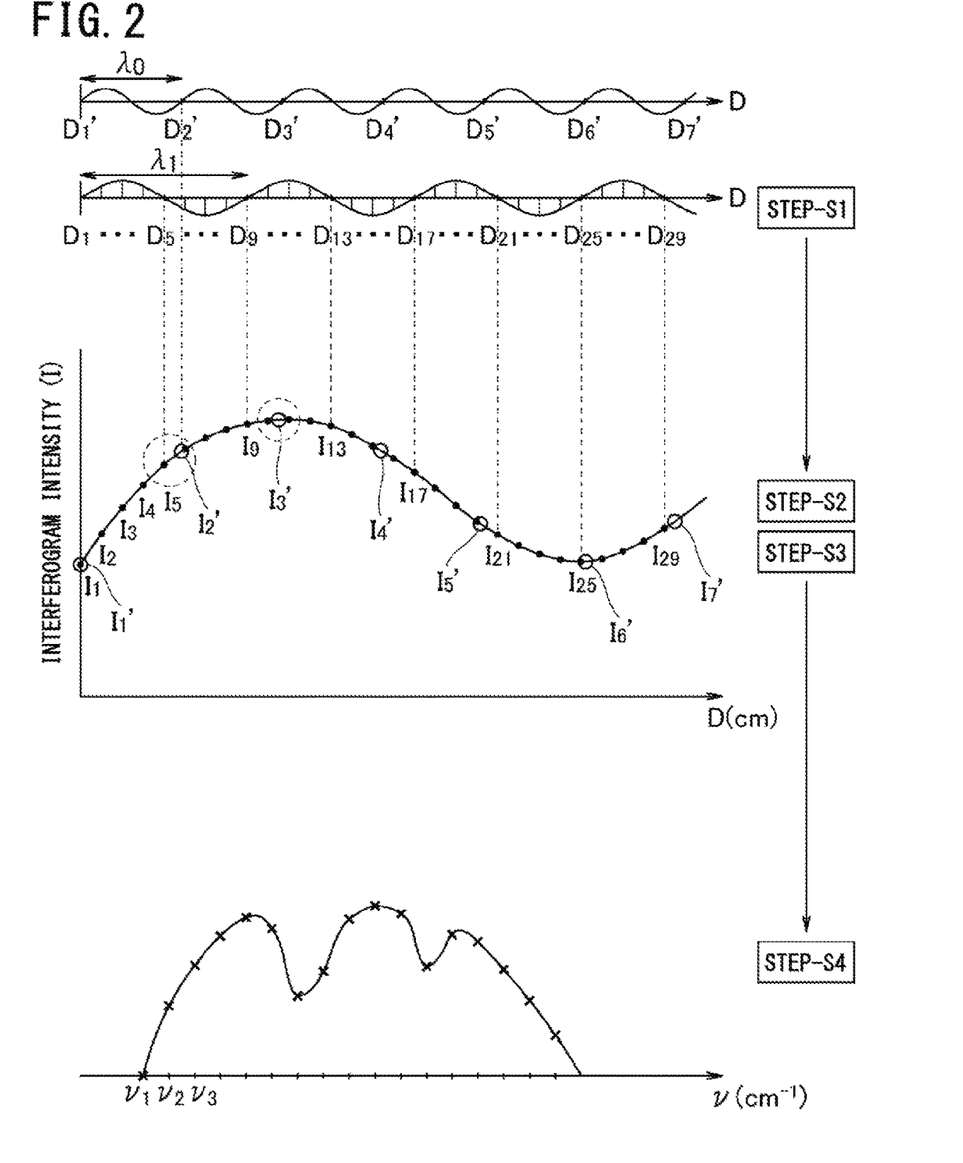
FIG. 2 is a diagram to describe a spectrum measurement method according to a first embodiment.

Next, in a step S2, the interferogram obtaining means 16 over-samples the intensity signal of the infrared interference wave at the above-mentioned detection timing. FIG. 2 shows the intensity signals (I1, I2, . . . ) of the infrared interference wave that is detected as the movable mirror moves every one eighth of the wavelength $\lambda 1$ ($\lambda \frac{1}{8}$). These are shown with black circles on the curve of the step S2 in FIG. 2.

In a step S3, the interferogram obtaining means 16 interpolates the intensity signal (I1', I2', . . . ) that would be obtained when the infrared interference wave is sampled at each position (D1', D2', . . . ) of the movable mirror 24 set on the basis of the wavelength $\lambda 0$ of the He—Ne laser, by using the over-sampling values (I1, I2, . . . ) actually detected at the step S2. The interferogram obtaining means 16 calculates each position (D1', D2', . . . ) of the movable mirror 24 set on the basis of the wavelength $\lambda 0$, based on a mirror position information from the position detecting means 34, the value of the wavelength $\lambda 0$ (632.8 nm), and the value of the wavelength $\lambda 1$ (680 nm). Then, in the interpolation process, the interferogram obtaining means 16 extracts a sampling position closest to each position (D1', D2', . . . ) and a sampling position second closest from the over-sampling positions (D1, D2, . . . ) at the step S2, and calculates the intensity signals (I1', I2', . . . ) that takes these position relationships into account based on each intensity signal at the sampling positions. For example, the intensity signal I2' in FIG. 2 is an interpolation value based on over-sampling values I5, I6, and the intensity signal I3' is an interpolation value based on over-sampling values I10, I11. In such way, the interferogram data composed of the intensity signals (I1', I2', . . . ) of the infrared interference wave at each position (D1', D2', . . . ) set on the basis of the wavelength $\lambda 0.0$ can be obtained. These are shown with circles on the curve at the step S3 of FIG. 2.

The positions (D1', D2', . . . ) set on the basis of the wavelength $\lambda 0$ are positions at fixed intervals from a position where the optical difference D becomes zero like the positions (D1, D2, . . . ) that are actually sampled. This fixed interval is a length of N times (or one Nth of) the wavelength $\lambda 0$. However, for execution of down-sampling at the step S3, a pitch of the positions (D1', D2', . . . ) set on the basis of the wavelength $\lambda 0$ is preferably bigger than a pitch at over-sampling positions (D1, D2, . . . ). This is because the interpolation value of the step S3 is calculated from the over-sampling value of the sampling position that is closer to each position set on the basis of the wavelength $\lambda 0$.

A detection interval of over-sampling is preferably set at an interval such that the interferogram does not change rapidly at such detection interval. For example, a sampling frequency is preferably higher than a frequency of increase/decrease of the interferogram along the optical path difference axis.

Finally, in a step S4, the Fourier transform means 18 Fourier-transforms the interferogram data calculated at the step S3 into the spectrum data of the sample.

In the interpolation process at the step S3, it is preferable that the computer uses a set value of the wavelength $\lambda 1$ stored in the memory 38 as the wavelength $\lambda 1$, not a constant value (680 nm). That is, it is preferable that the computer uses the set value of the memory 38 that is updated to a value of the wavelength $\lambda 1$ after validation by execution of the step of validating the wavelength $\lambda 1$ in case the wavelength $\lambda 11$ of the semi-conductor laser 30 is changed.

When the computer executes the above-mentioned data process program, the interferogram at the same mirror position as when the interferogram is obtained by the He—Ne laser as the position reference laser is calculated. As a result, the spectrum data measured by the spectroscopic device that comprises the semi-conductor laser becomes substantially identical to the spectrum measured by the spectroscopic device that comprises the He—Ne laser, and thus spectrum comparison with numerous reference spectrum data that are stored becomes possible.

<Validation Program>

Moreover, a program to validate the wavelength $\lambda 1$ of the semi-conductor laser 30 in case the wavelength $\lambda 1$ of the semi-conductor laser 30 changes over time (or by environmental dependence) is described. This program refers to a reference spectrum data obtained by measuring the reference sample by the conventional spectroscopic device that comprises the He—Ne laser of the wavelength $\lambda 0$. The spectroscopic device of the present embodiment may measure such the reference spectrum data of the wavelength $\lambda 0$ each time, but it is preferable that the spectroscopic device reads out the reference spectrum data of the wavelength $\lambda 0$ that is stored in the memory 38 in advance as necessary.

Figure 3:
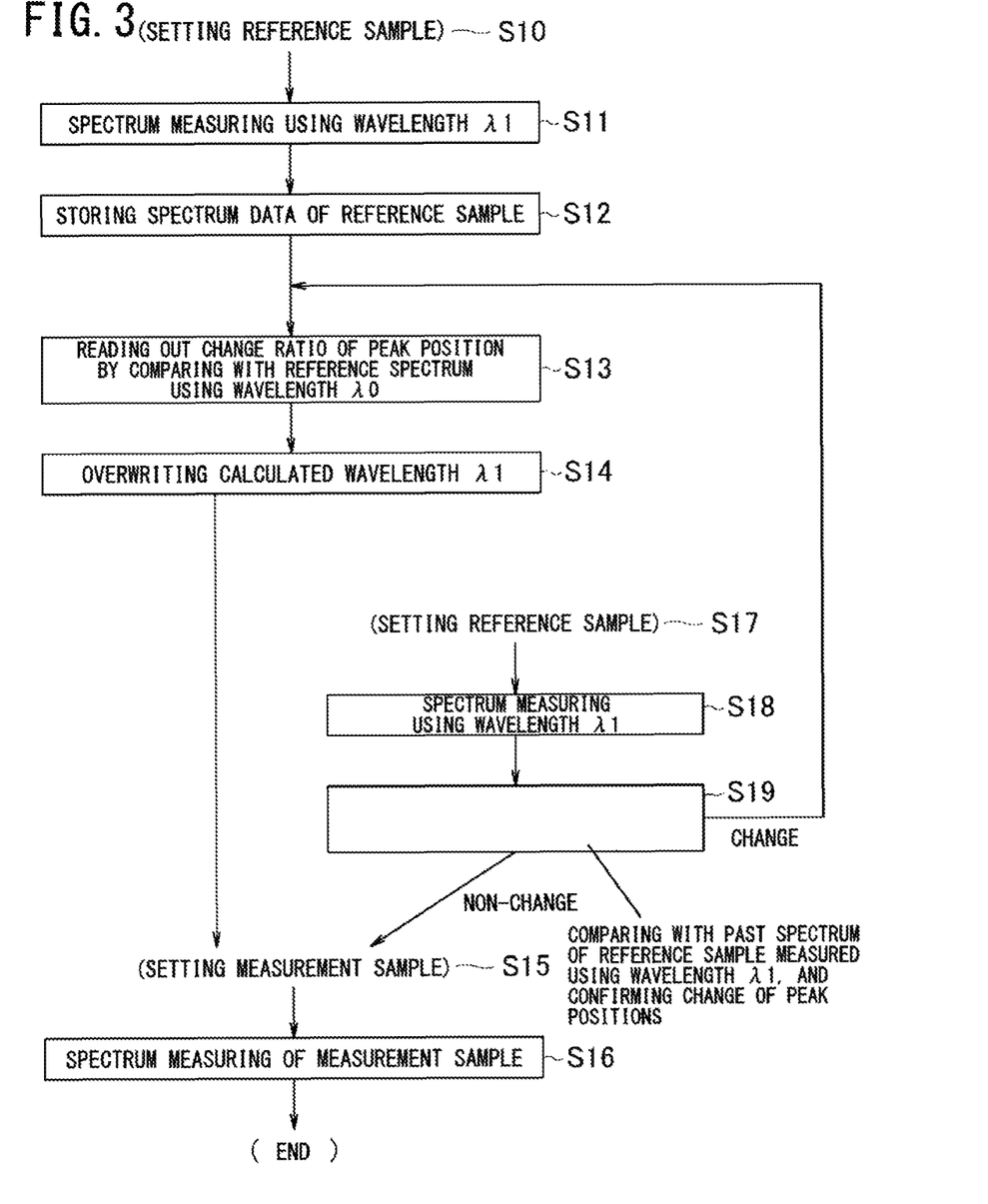
FIG. 3 is a flow chart to describe a validation method of a laser wavelength in the spectrum measurement method.

As shown in the flow of FIG. 3, the validation program makes the computer that constitutes the interferogram obtaining means 16 and the Fourier transform means 18 to execute spectrum measurement to the reference sample. That is, the reference sample holder 26*a* is set in a sample chamber (step S10), and, in accordance with the above-mentioned steps S1 to S4, the spectroscopic device executes spectrum measurement that uses the semi-conductor laser 30 having the wavelength $\lambda 1$ (step S11). The Fourier transform means 18 stores the measurement spectrum data by the wavelength $\lambda 1$ to the memory 38 (step S12). In the memory 38, information regarding peak positions of the spectrum and the like are stored, too.

Next, in a step S13, the Fourier transform means 18 compares the spectrum data of the reference sample by the wavelength $\lambda 1$ measured at the step S11 and the reference spectrum data by the wavelength $\lambda 0$ in the memory 38. The computer reads out change ratio of each peak position with respect to a plurality of peaks in the spectrum, and obtains an average value of change ratio. For example, when the wavelength $\lambda 1$ of the semi-conductor laser is minutely changed to the wavelength $\lambda 1'$, change ratio of the peak position is expressed as "$\lambda 1'/\lambda 1$". In a step S14, the computer recalculates the wavelength $\lambda 1$ of the semi-conductor laser 30 based on the average value of change ratio, and overwrites this value of the wavelength $\lambda 1$ to the memory 38.

Validation of the laser wavelength $\lambda 1$ is completed in the above-mentioned steps. In the following spectrum measurement, the sample holder 26 of the measurement sample is set (step S15), and the interferogram obtaining means 16 obtains the interferogram based on the validated wavelength $\lambda 1$, so that the spectroscopic device can obtain spectrum data that is not affected by the change of the wavelength $\lambda 1$ (step S16).

A method to use information of the peak position of the spectrum data of the reference sample by the wavelength $\lambda 1$ that is stored in the memory 38 at the step S12 is described herein. Before spectrum measurement of the measurement sample of steps S15, S16, the reference sample is set (step S17), and spectrum measurement of the reference sample by the wavelength $\lambda 1$ like the spectrum measurement step S11 (step S18) is executed. The peak position of the measurement spectrum by the wavelength $\lambda 1$ and the past peak position of the spectrum by the wavelength $\lambda 1$ stored in the memory 38 are compared, and if there is a change in peak positions, it is determined that the wavelength λ1 of the semi-conductor laser 30 is changed (step S19). When the change of the wavelength λ1 is confirmed, the above-mentioned validation of the wavelength λ1 is executed (steps S13, S14).

The spectrum measurement method of the present embodiment includes a step of interpolation process of the interferogram. There is a possibility that a value different from the true value of the interferogram (false information) is produced by this process, and S/N will be deteriorated in theory. However, the level of S/N (for example, 200,000:1) of these false information is extremely small with respect to the level of S/N ratio required for measurement devices (for example, 50,000:1), and thus effect on measurement result will be extremely small.

Second Embodiment

Although the above-mentioned embodiment includes the execution program of over-sampling, a data process program of the present embodiment does not execute over-sampling in order to achieve high-speed process. The configuration of the spectroscopic device is in common with the above-mentioned embodiment.

<Data Process Program>

To obtain spectrum data of the sample, the data process program of the present embodiment makes the computer that constitutes the interferogram obtaining means 16 and the Fourier transform means 18 to execute the following steps S21 to S24.

First of all, in a step S21 (refer to FIG. 4), the interferogram obtaining means 16 obtains position information (D1, D2, . . . ) of the movable mirror 24 based on the general-purpose laser of the wavelength λ1 from the position detecting means 34.

Figure 4:
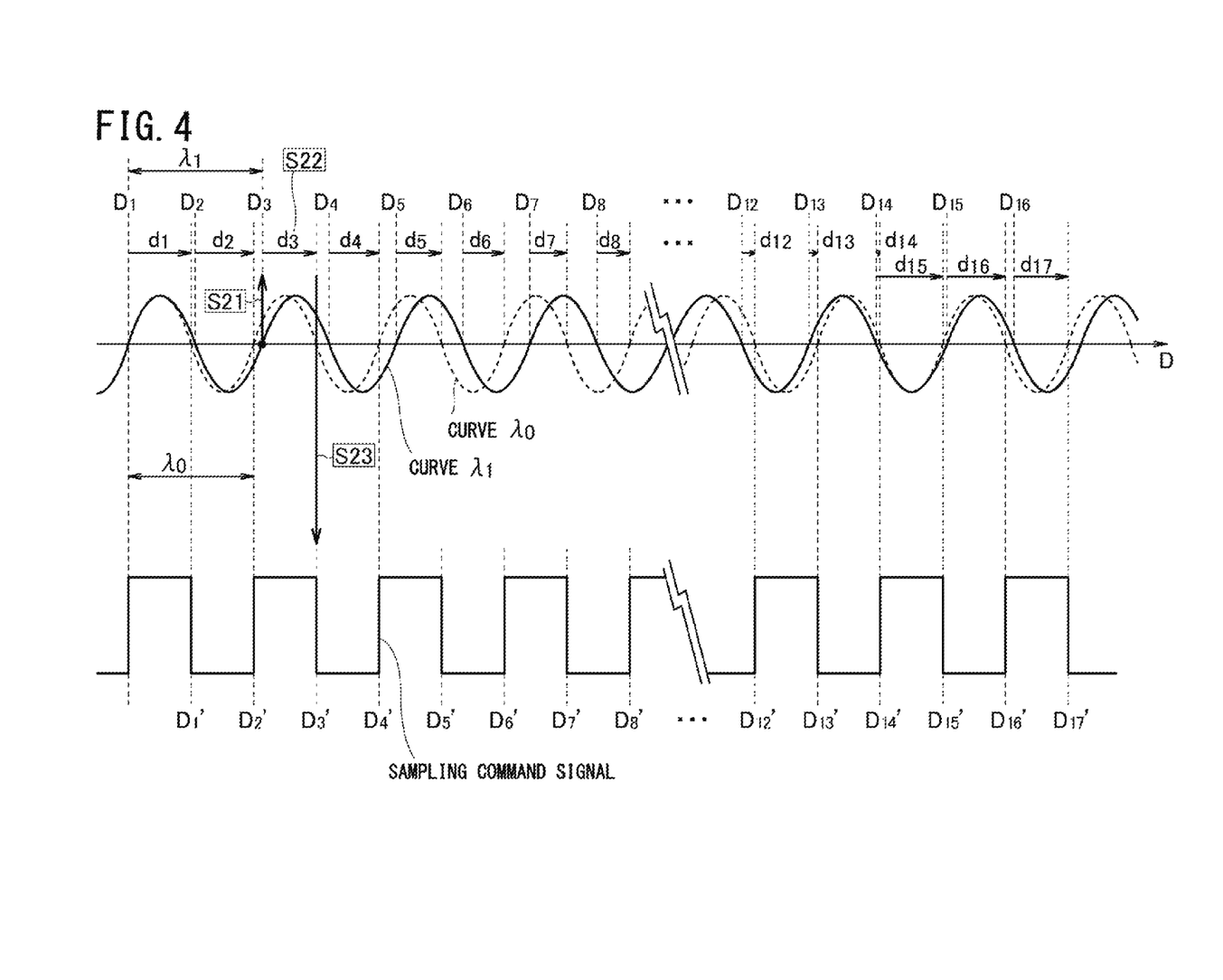
FIG. 4 is a diagram to describe a method of generating a sampling command signal in the spectrum measurement method according to a second embodiment.

In a step S22, the interferogram obtaining means 16 uses position information of the movable mirror 24, and calculates each sampling position (D1', D2', . . . ) of the movable mirror 24 that would be obtained when the wavelength λ0 of the reference laser is used as a reference. More specifically, the interferogram obtaining means 16 regards the timing that respective predetermined delay time (t1, t2, . . . ) has passed from the timing of which the movable mirror 24 reaches each position (D1, D2, . . . ) set on the basis of the wavelength λ1 as each sampling position (D1', D2', . . . ) of the movable mirror 24 set on the basis of the wavelength λ0, and emits a sampling command signal at that timing (step S23).

The position information (D1, D2, . . . ) based on the general-purpose laser of the wavelength λ1 shows the positions at fixed intervals from the position of the movable mirror 24 where the optical difference D of the interferometer 12 becomes zero. This fixed interval is a length of N times (or one Nth of) the wavelength λ1.

Positions (D1+d1, D2+d2, . . . ) that are obtained by adding certain lengths (d1, d2, . . . ) to the positions (D1, D2, . . . ) set on the basis of the wavelength λ1 become the sampling positions (D1', D2', . . . ) of the movable mirror set on the basis of the wavelength λ0. The certain lengths (d1, d2, . . . ) are gained by multiplying the moving speed of the movable mirror 24 by the delay time (t1, t2, . . . ).

If the movable mirror 24 is controlled at a constant speed, the moving speed of the movable mirror 24 will be maintained at a fixed value (V0), so that the delay time (t1, t2, . . . ) can be calculated form the lengths (d1, d2, . . . ).

FIG. 4 shows an example of a case when intervals of position information (D1, D2, . . . ) are half value of the wavelength λ1. The lengths (d1, d2, . . . ) of when λ0=623.8 nm and λ1=680 nm are expressed by the following equations.

$$d1 = \lambda1/2 - (\lambda1 - \lambda0)/2$$
$$= 340 \text{ nm} - 23.6 \text{ nm} = 316.4 \text{ nm}$$
$$d2 = d1 - 23.6 \text{ nm} = 292.8 \text{ nm}$$
$$d3 = d2 - 23.6 \text{ nm} = 269.2 \text{ nm}$$

For example, when the movable mirror 24 reaches the position D3 (step S21), the computer issues a sampling command of the position D3' (step S23) at a timing of which a delay time t3 (=d3/V0) has passed from the timing that the movable mirror 24 reached the position D3 (step S22).

However, when the length is d≤(λ1−λ0)/2, that is d≤23.6, the next delay time t becomes a negative value. Therefore, the computer calculates the sampling position by the value of d, and, at the same time, uses another value gained by adding λ0/2 (=316.4 nm) to d as a new value of d to calculate another sampling position by the new value of d. As shown in FIG. 4, when d14=9.6 nm, the computer determines the sampling position of D14' by calculating D14+d14, and also calculates the sampling position of D15' by the value of d15. The computer determines d15 based on the equation of d15=9.6+316.4=326 nm, and calculates the sampling position of D15' based on the equation of D15'=D14+d15 set on the basis of the position D14.

In the step S22, the delay time (t1, t2, . . . ) is calculated based on the calculated value of the lengths (d1, d2, . . . ) and the moving speed (V0). Then, in the step S23, the spectroscopic device samples the intensity signal of the infrared interference wave at a timing that the movable mirror 24 is regarded to have reached the sampling positions (D1', D2', . . . ). Accordingly, the interferogram composed of the intensity signals (I1', I2', . . . ) of the infrared interference wave at the sampling positions (D1', D2', . . . ) set on the basis of the wavelength λ0 of the He—Ne laser can be obtained.

When the interval of the position information (D1, D2, . . . ) is a quarter of the wavelength λ1, the lengths (d1, d2, . . . ) can be obtained from a similar calculation.

$$d1 = \lambda1/4 - (\lambda1 - \lambda0)/4$$
$$= 170 \text{ nm} - 11.8 \text{ nm} = 158.2 \text{ nm}$$

$$d2 = d1 - 11.8 \text{ nm} = 146.4 \text{ nm}$$

$$d3 = d2 - 11.8 \text{ nm} = 134.6 \text{ nm}$$

Finally, in the step S24, the Fourier transform means 18 Fourier-transforms the obtained interferogram data into the spectrum data of the sample.

So far, cases when the moving speed of the movable mirror 24 is regarded to be constant have been described. It is preferable that the data process program of the present embodiment includes a step of calculating the moving speed V of the movable mirror 24 at a point when the movable mirror 24 reaches each position (D1, D2, . . . ) set on the basis of the wavelength λ1. Since the method of the present embodiment includes measurement of the delay time, the sampling position is shifted when constancy of speed of the movable mirror 24 cannot be secured for some reason. In such case, the position detecting means 34 measures the interval of past zero-cross points by the semi-conductor laser, and the computer calculates the speed of the movable mirror 24, so that the next sampling position is compensated at that calculated speed.

By using the above-described data process program, the interferogram at a same mirror position as the case when the interferogram is obtained by the He—Ne laser used as the position reference laser is calculated. As a result, the spectrum data measured by the spectroscopic device comprising the semi-conductor laser becomes substantially identical to the spectrum measured by the spectroscopic device comprising the He—Ne laser, and spectrum comparison that uses numerous reference spectrum data that are stored becomes possible.

When over-sampling, data process of Fourier-transforming all of the interferogram of 100 data or more in one second, for example, is not practical because great amount of calculation resource such as a calculator and the like have to be used. According to the method of the present embodiment, the interferogram at a timing relatively close to the detection timing of the He—Ne laser is obtained without over-sampling. As a result, calculation load can be reduced, and reproductive data can be obtained.

Validation of the wavelength $\lambda 1$ in the above-mentioned embodiment can also be applied to spectrum measurement in the second embodiment.

What is claimed is:

1. A method for measuring spectrum of sample comprising:
   a step of obtaining an interferogram of a measurement light with an interferometer, and
   a step of Fourier-transforming the interferogram into a spectrum of a sample,
   wherein the step of obtaining the interferogram comprises:
     a step of moving a movable mirror that constitutes the interferometer at a constant speed,
     a step of over-sampling intensity signals (I1, I2, . . . ) of an interference wave of the measurement light at positions (D1, D2, . . . ) of the movable mirror set on the basis of a wavelength $\lambda 1$ by using a general-purpose laser of the wavelength $\lambda 1$ as a position reference laser of the movable mirror, and
     a step of interpolating intensity signals (I1', I2', . . . ) that would be obtained when the interference wave of the measurement light is sampled at positions (D1', D2', . . . ) of the movable mirror set on the basis of a wavelength $\lambda 0$ that is different from the wavelength $\lambda 1$, based on the over-sampled intensity signals (I1, I2, . . . ) by a computer,
   wherein the interferogram comprising the intensity signals (I1', I2', . . . ) of the interference wave of the measurement light at positions (D1', D2', . . . ) of the movable mirror set on the basis of the wavelength $\lambda 0$ is obtained.

2. The method according to claim 1, wherein the step of interpolating includes calculating the intensity signal (I1', I2', . . . ) of the interference wave at the position of the movable mirror set on the basis of the wavelength $\lambda 0$, based on intensity signals that are over-sampled at sampling positions that are the closest and the second closest to the position of the movable mirror set on the basis of the wavelength $\lambda 0$ by the computer.

3. The method according to claim 1 further comprising:
   a step of validating the wavelength $\lambda 1$ of the general-purpose laser,
   wherein the step of validating comprises:
     a step of measuring a spectrum of a reference sample by an interferometer having a reference laser of a wavelength $\lambda 0$ as the position reference laser,
     a step of measuring a spectrum of the reference sample by an interferometer having a general-purpose laser of a wavelength $\lambda 1$ as the position reference laser, and
     a step of calculating the wavelength $\lambda 1$ of the general-purpose laser based on an average value of change ratio of each peak position for a plurality of peaks in the spectrum, wherein the change ratio of each peak position is read out by comparing two spectra measured at two steps of measuring.

4. The method according to claim 3 further comprising:
   a step of storing the peak positions of the spectrum of the reference sample measured by the interferometer having the general-purpose laser of the wavelength $\lambda 1$ to a memory means; and
   a step of comparing the stored peak position of the spectrum of the reference sample and the peak position of the spectrum of the reference sample measured afterwards,
   wherein the step of validating is performed when the peak positions of the two spectra are changed.

5. A method for measuring spectrum of sample comprising:
   a step of obtaining an interferogram of a measurement light with an interferometer, and
   a step of Fourier-transforming the interferogram into a spectrum of a sample,
   wherein the step of obtaining the interferogram comprises:
     a step of moving a movable mirror that constitutes the interferometer at a constant speed, and
     a step of sampling intensity signals (I1', I2', . . . ) of an interference wave of the measurement light at positions (D1', D2', . . . ) of the movable mirror set on the basis of a wavelength $\lambda 0$ that is different from a wavelength $\lambda 11$ by using a general-purpose laser of the wavelength $\lambda 1$ as a position reference laser of the movable mirror,
   wherein the interferogram comprised of the intensity signals (I1', I2', . . . ) of the interference wave of the measurement light at sampling positions (D1', D2', . . . ) set on the basis of the wavelength $\lambda 0$ is obtained.

6. The method according to claim 5, wherein, in the step of sampling, each position of the movable mirror at a timing of which a delay time respectively determined for each position of the movable mirror passes from a timing when the movable mirror reaches each position set on the basis of the wavelength $\lambda 1$ is used as the each sampling position (D1', D2', . . . ) set on the basis of the wavelength $\lambda 0$.

7. The method according to claim 5, wherein, in the step of sampling, each position of the movable mirror obtained by adding a certain length to each position set on the basis of the wavelength $\lambda 1$ is used as the each sampling position (D1', D2', . . . ) set on the basis of the wavelength $\lambda 0$,
   wherein the certain length is gained by multiplying a moving speed of the movable mirror by a delay time respectively determined for each position of the movable mirror.

8. The method according to claim 7 further comprising:
   a step of detecting the moving speed of the movable mirror for each point when the movable mirror reaches each position (D1, D2, . . . ) set on the basis of the wavelength $\lambda 1$, wherein, in the step of sampling, the each sampling position (D1', D2', . . . ) set on the basis of the wavelength λ0 is calculated by the detected moving speed.

* * * * *

UNITED STATES PATENT AND TRADEMARK OFFICE
CERTIFICATE OF CORRECTION

PATENT NO. : 10,317,283 B2
APPLICATION NO. : 16/075346
DATED : June 11, 2019
INVENTOR(S) : Sunami et al.

It is certified that error appears in the above-identified patent and that said Letters Patent is hereby corrected as shown below:

In the Claims

Column 14, Line 41 (Claim 5, Line 14) please change "$\lambda 11$" to -- $\lambda 1$ --.

Signed and Sealed this
Twenty-fifth Day of February, 2020

Andrei Iancu
*Director of the United States Patent and Trademark Office*